(12) United States Patent
Crawford et al.

(10) Patent No.: US 6,743,186 B2
(45) Date of Patent: Jun. 1, 2004

(54) BLOOD COLLECTION ASSEMBLY

(75) Inventors: Jamieson William Maclean Crawford, New York, NY (US); Stefanie Livanos, Bethlehem, PA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 96 days.

(21) Appl. No.: 10/054,234

(22) Filed: Nov. 13, 2001

(65) Prior Publication Data

US 2002/0111566 A1 Aug. 15, 2002

Related U.S. Application Data

(60) Provisional application No. 60/259,876, filed on Jan. 5, 2001.

(51) Int. Cl.[7] ................................................. A61B 5/00
(52) U.S. Cl. ........................ 600/583; 604/192; 604/198
(58) Field of Search ................................ 600/573, 576, 600/583; 604/110, 157, 164.01, 165.01, 165.02, 165.03, 165.04, 192, 194, 195, 198

(56) References Cited

U.S. PATENT DOCUMENTS

| | | | | |
|---|---|---|---|---|
| 4,349,022 A | * | 9/1982 | Ishikawa | 604/180 |
| 4,894,055 A | * | 1/1990 | Sudnak | 604/198 |
| 5,354,281 A | * | 10/1994 | Chen | 604/177 |
| 5,591,138 A | * | 1/1997 | Vaillancourt | 604/263 |
| 5,779,679 A | | 7/1998 | Shaw | 604/158 |
| 5,800,404 A | * | 9/1998 | Poulsen | 604/198 |
| 6,210,371 B1 | | 4/2001 | Shaw | 604/164.08 |

* cited by examiner

Primary Examiner—Charles Marmor
Assistant Examiner—Jonathan Foreman
(74) Attorney, Agent, or Firm—Nanette S. Thomas, Esq.; Scott J. Rittman, Esq.

(57) ABSTRACT

An automatically shieldable blood collection set is provided. The blood collection set includes a needle assembly having a hub with spaced apart inner and outer tubes. A needle cannula is fixedly attached to the inner tube. A safety shield is telescoped for movement into the space between the inner and outer tubes of the hub. The safety shield can be moved from a proximal position where the needle cannula is exposed to a distal position where the needle cannula is safely shielded. A spring is provided between the shield and the hub to propel the shield distally relative to the hub and into surrounding relationship with the needle cannula. A retainer is provided for releasably holding the shield in a proximal ready-to-use condition relative to the hub and the needle cannula. The retainer may be provided on a fin that extends transversely from the outer tube of the hub. An actuator releases the retainer and enables the shield to be propelled by the spring. The actuator may define portions of the wing spaced from the retainer. A lock may be provided for preventing inadvertent re-exposure of the needle cannula.

6 Claims, 2 Drawing Sheets

BLOOD COLLECTION ASSEMBLY

This application claims the benefit of Provisional Application No. 60/259,876, filed Jan. 5, 2001.

BACKGROUND OF THE INVENTION

1. Field of the Invention

The subject invention relates to a blood collection set having a needle cannula and a shield that can be driven forwardly to safely shield the needle cannula.

2. Description of the Related Art

A prior art blood collection set includes a small diameter needle cannula having a pointed distal end and a proximal end mounted to a thermoplastic hub. Portions of the blood collection set near the hub may be provided with a pair of flexible wings. The wings can be folded into face-to-face engagement with one another to facilitate digital manipulation of the small needle cannula. The wings then can be folded away from one another and taped into face-to-face engagement with the skin of the patient near a puncture site. The prior art blood collection set further includes a flexible plastic tube that has one end connected to the hub and an opposed end connected to a fitting. The fitting can be placed in communication with a reservoir to which collected blood may be directed.

The needle cannula of the prior art blood collection set typically is shielded prior to and after use to prevent accidental sticks. Needle shields used with prior art blood collection sets have taken many forms. Typically, a prior art blood collection set is packaged with a rigid tubular cap telescoped over the needle cannula to prevent accidental sticks prior to use. This tubular cap is removed from the needle cannula immediately prior to use of the blood collection set. Most prior art blood collection sets further include a second shield that is telescoped over the needle cannula and hub. The second shield may include at least one slot through which wings of the prior art hub may extend. Thus, the medical technician who uses the prior art blood collection set will hold the wings of the needle hub in one hand and the shield in the other hand after removing the needle cannula from the patient or blood donor. The wings then are slid proximally relative to the shield, thereby drawing the needle cannula into the shield. Some prior art shields are configured to engage the wings when the needle cannula has been shielded to make a re-exposure of the needle cannula difficult.

The digital manipulation that is required to shield the used needle cannula of a prior art blood collection set creates the potential for generating the accidental needle stick that the shield is intended to avoid. In particular, it is undesirable to rely upon a shielding that requires two hands to be moved in opposite directions in proximity to the point of a used needle cannula. Accordingly, the inventors herein have recognized the desirability of providing an automatically shieldable needle cannula for a blood collection set.

SUMMARY OF THE INVENTION

The subject invention relates to a blood collection set which comprises a needle cannula having a proximal end, a pointed distal end and a lumen extending therebetween.

The blood collection set further includes a hub that may be molded from a thermoplastic material. The hub includes opposite proximal and distal ends. The hub further includes concentric spaced apart inner and outer tubes extending between the proximal and distal ends. The inner and outer tubes are connected to one another at their respective proximal ends. However, the inner and outer tubes of the hub are not connected at the distal end. Thus, a cylindrical space extends proximally from the distal end of the hub and between the inner and outer tubes. A passage extends continuously between the proximal and distal ends of the inner tube of the hub. The distal end of the inner tube of the hub is securely mounted to the proximal end of the needle cannula. Thus the lumen through the needle cannula communicates with the passage through the inner tube of the hub.

A pair of deflectable fins projecting transversely from opposite sides of the outer tube of the hub at locations adjacent the distal end of the outer tube. The fins can be rotated toward one another about the outer tube and into a position where the rotated fins can be engaged by a thumb and forefinger for gripping and manipulating the blood collection set. At least one of the fins further includes a projection that extends at least partly across the opening between the inner and outer tubes at the distal end of the hub when the fins project transversely from the outer tube. However, rotation of the fins toward one another will cause the projection to rotate away from the opening to the cylindrical space between the inner and outer tubes.

The hub may further include a dorsal fin that projects radially outwardly from the outer tube at a location adjacent the distal end of the hub. The transverse fins can be rotated into engagement against the dorsal fin. Thus, the dorsal fin permits manipulation of the blood collection set when the transverse fins are in their unbiased condition and extending away from one another. However, the transverse fins can be rotated toward one another and into engagement with opposite surfaces of the dorsal fin. Thus, a user can simultaneously grip the transverse fins and the dorsal fin for manipulating the blood collection set. The outer tube may further include at least one locking aperture extending through the outer tube at a location near the distal end of the outer tube.

The blood collection set may further include a length of flexible tubing having opposed proximal and distal ends. The distal end of the flexible tubing may be connected to the proximal end of the hub such that the lumen through the needle cannula and the passage through the hub both communicate with the passage through the flexible tubing. The flexible tubing further includes a proximal end that may be connected to a fitting. The fitting may comprise a needle cannula that enables the blood collection set to be placed in communication with a reservoir for receiving a sample of blood. The tubing and the fitting may be of conventional design.

The blood collection set may further include a substantially rigid generally tubular safety cap mounted over the needle cannula for protection against accidental needle sticks prior to use of the blood collection set. The safety cap may include a proximal end that is frictionally engaged with the hub. The rigid tubular safety cap may be removed immediately prior to use of the blood collection set.

The blood collection set further includes a safety shield that is telescoped over at least portions of the inner tube of the hub and cannula and at least partly within the outer tube. Thus, the safety shield is movable within the cylindrical space between the inner and outer tubes of the hub from a proximal position, where the needle cannula is exposed, to a distal position, where the needle cannula is safely shielded. Biasing means are provided between the shield and the hub for urging the shield to the distal position. The biasing means may be a coil spring that surrounds a portion of the inner tube of the hub.

The projections on the transverse fins function as a retainer for releasably retaining the shield in the proximal position relative to the hub and the needle cannula and against the stored energy of the biasing means. Rotation of the transverse fins towards one another and/or toward the dorsal fin moves the projections of the transverse fins away from the opening to the cylindrical space between the inner and outer tubes of the hub. Thus, the safety shield is free to move in response to the stored energy of the biasing means. The safety shields and the hub may further include a lock for preventing complete removal of the safety shield from the hub when the transverse fins are moved into a position that permits the distal movement of the shield. The lock may further prevent a return proximal movement that could re-expose the used needle cannula.

DETAILED DESCRIPTION

Figure 1:
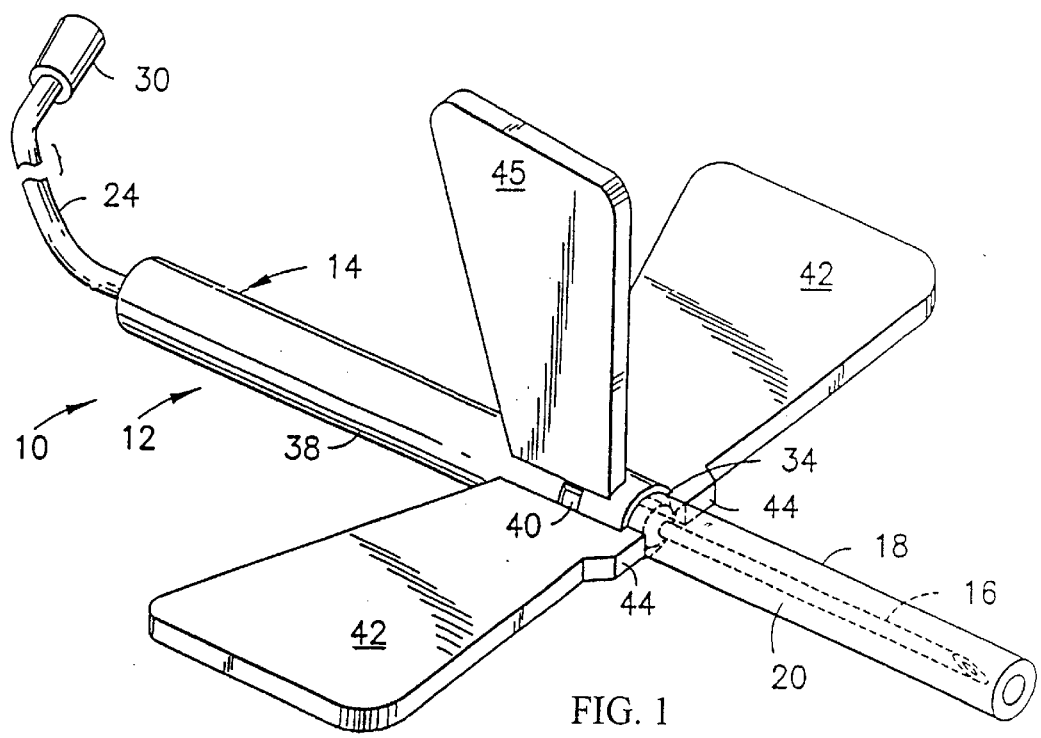
FIG. 1 is a perspective view of a blood collection set in accordance with the subject invention.
Figure 2:
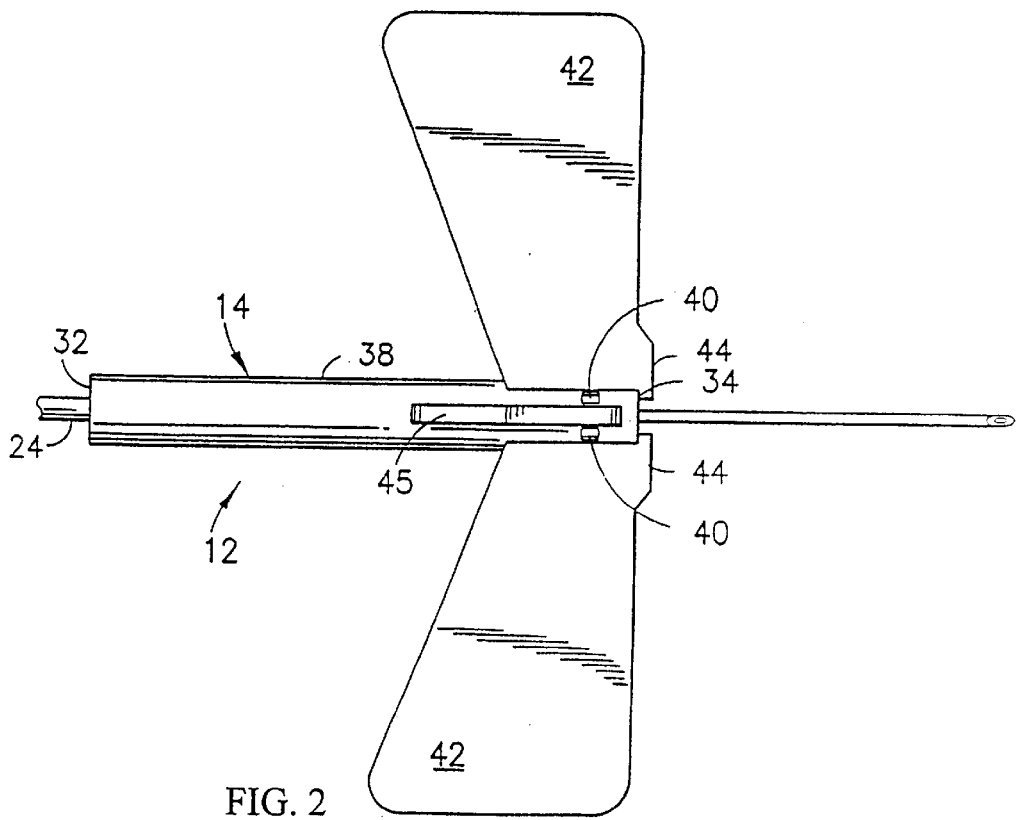
FIG. 2 is a top plan view of the needle assembly shown in FIG. 1 with the safety cap removed.
Figure 3:
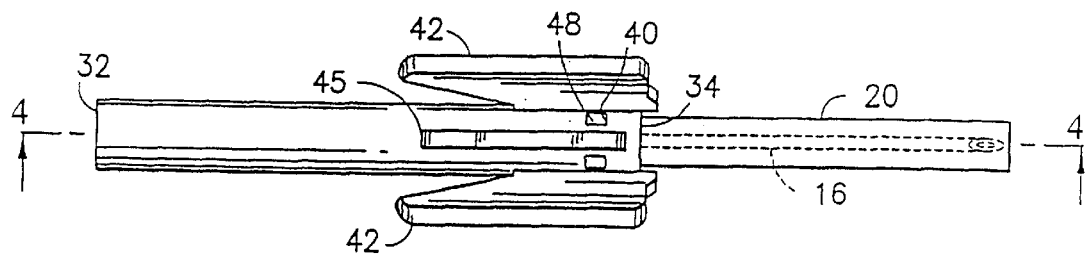
FIG. 3 is a top plan view similar to FIG. 2 but showing the shield after actuation by the wings.

A blood collection set in accordance with the subject invention is identified by the numeral 10 in FIGS. 1–4. Blood collection set 10 includes a needle assembly 12 with a hub 14, a needle cannula 16, a safety cap 18, a safety shield 20, and a spring 22. Blood collection set 10 also includes a flexible tube 24 and a fitting 30. Fitting 30 is configured to be placed in communication with a reservoir into which blood drawn by needle assembly 12 may be deposited.

Hub 14 includes an annular proximal wall 32, a distal end 34, a tubular inner wall 36 (FIG. 4) extending distally from proximal wall 32 and a tubular outer wall 38 extending distally from proximal wall 32. Outer wall 38 is in spaced concentric relationship to tubular inner wall 36. Portions of tubular inner wall 36 at distal end 34 of hub 14 are mounted to needle cannula 16 substantially as with the first embodiment. Outer wall 38 of hub 14 has an inwardly directed stop flange 39. Additionally, outer wall 38 is provided with a locking aperture 40 in proximity to distal end 34.

Outer wall 38 includes a pair of actuator wings 42 projecting transversely therefrom. Actuator wings 42 include retainer projections 44 extending toward needle cannula 16 and partly across outer wall 38 at distal end 34 of hub 14. As explained further herein, projections 44 retain safety shield 20 within outer wall 38. Actuator wings 42 can be rotated toward one another substantially as in the previous embodiment. However, such rotation of wings 42 moves projections 44 away from needle cannula 16 and out of blocking engagement with shield 20. Outer wall 38 includes a dorsal fin 45 projecting transversely therefrom and at a location separated from actuator wings 42 by approximately 90°.

Shield 20 initially is slidably disposed within outer wall 38 and in surrounding relationship to inner wall 36 of hub 14. Shield 20 can be moved from the proximal position shown in FIG. 2 to the distal position shown in FIGS. 3 and 4. Shield 20 defines a length sufficient to cover all of needle cannula 16 when shield 20 is in its distal position of FIGS. 3 and 4.

Figure 4:
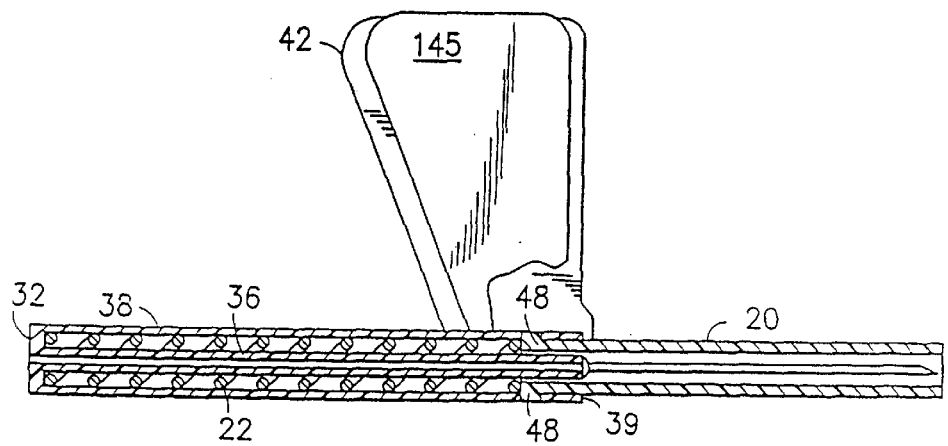
FIG. 4 is a cross-sectional view taken along line 4—4 in FIG. 3.

As shown most clearly in FIG. 4, shield 20 includes locking projections 48 at proximal end portions thereof. Locking projections 48 are dimensioned and disposed to lockingly engage stop flange 39 and locking aperture 40 when shield 20 is in its distal position. Spring 22 is disposed between proximal wall 32 of hub 14 and locking projections 48 of shield 20. Thus, in the ready-to-use condition of FIG. 2, spring 22 is in a compressed condition.

Needle assembly 12 is used by initially gripping dorsal fin 45 and then removing safety cap 18. Needle cannula 16 then is inserted into the patient to draw a sample of blood. Needle assembly 12 then can be gripped by dorsal fin 45 to remove needle cannula 16 from the patient. Upon removal, actuator wings 42 are rotated toward one another. This rotation causes retainer projections 44 to rotate away from shield 20, and thereby removes blocking forces that had been exerted on shield 20. As a result, spring 22 is released and propels shield 20 distally and into shielding engagement over needle cannula 16. After sufficient distal movement, locking projections 48 at the proximal end of shield 20 will engage stop flange 39 of outer wall 38. Simultaneously, locking projections 48 will engage in lock aperture 40. Thus, shield 20 is locked in a distal position protectively surrounding needle cannula 16.

What is claimed is:

1. A needle assembly comprising:
   a hub having opposite proximal and distal ends, inner and outer tubes extending from the proximal end and to the distal end, a substantially cylindrical space being defined between the inner and outer tubes and being open at the distal end of the hub, the inner and outer tubes being connected to one another at the proximal end of the hub, a passage extending through the inner tube from the proximal end to the distal end;
   a needle cannula having a proximal end rigidly connected to said distal end of said inner tube of said hub, a distal end and a lumen extending therebetween, said lumen providing fluid communication with said passage through said inner tube of said hub;
   a shield telescoped within said outer tube of said hub and telescoped over said inner tube of said hub and said needle cannula and movable from a proximal position where said needle cannula is exposed to a distal position where said needle cannula is shielded;
   a spring captured between portions of said hub and said shield and being operative for propelling said shield into said distal position relative to said hub and said needle cannula;
   a retainer for releasably retaining the shield in the proximal position; and
   an actuator for selectively releasing said retainer,
   wherein said actuator comprises at least one resiliently deflectable wing extending outwardly from portions of said outer tube adjacent said distal end of said hub, said wing being rotationally deflectable about said outer tube, said retainer being joined to said wing and being movable in response to deflection of said wing from a first position where said retainer blocks said shield and a second position where said retainer permits movement of said shield into said distal position,
   wherein in the initial state of the assembly prior to use, said cannula is exposed, said shield is located in said proximal position, and said assembly further comprises a safety cap disposed over at least a portion of the exposed needle cannula.

2. The needle assembly of claim 1, further comprising a lock for locking said shield in said distal position.

3. The needle assembly of claim 1, wherein said retainer is a first retainer, said needle assembly further comprising a second retainer, a second wing being rotatably connected to said outer tube and being connected to said second retainer such that rotation of said wings toward one another simultaneously moves said retainers into a position for permitting said spring to propel said shield into said distal position.

4. The needle assembly of claim 3, further comprising a dorsal fin connected to said outer tube of said hub at a location intermediate said wings.

5. The needle assembly of claim 1, further comprising a flexible tube extending from the proximal end of the hub and communicating with the passage through the inner tube of the hub.

6. The needle assembly of claim 5, further comprising a fitting securely mounted to an end of the flexible tube remote from the needle assembly.

* * * * *